(12) United States Patent
Heo et al.

(10) Patent No.: US 11,067,564 B2
(45) Date of Patent: Jul. 20, 2021

(54) PORTABLE INSULIN RESISTANCE DIAGNOSIS DEVICE AND DIAGNOSIS METHOD USING SAME

(71) Applicants: INDUSTRY ACADEMIC COOPERATION FOUNDATION KEIMYUNG UNIVERSITY, Daegu (KR); KOREA ADVANCED INSTITUTE OF SCIENCE AND TECHNOLOGY, Daejeon (KR)

(72) Inventors: Yun Seok Heo, Daegu (KR); Dae-Kyu Song, Daegu (KR); Su Jeong Shin, Daejeon (KR); Min Ho Yang, Daejeon (KR); Jae-hoon Han, Gyeryong-si (KR); Tae Jae Lee, Cheongju-si (KR); Seok Jae Lee, Daejeon (KR)

(73) Assignees: INDUSTRY ACADEMIC COOPERATION FOUNDATION KEIMYUNG UNIVERSITY, Daegu (KR); KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 447 days.

(21) Appl. No.: 15/570,362

(22) PCT Filed: Apr. 29, 2016

(86) PCT No.: PCT/KR2016/004551
§ 371 (c)(1),
(2) Date: Oct. 30, 2017

(87) PCT Pub. No.: WO2016/175615
PCT Pub. Date: Nov. 3, 2016

(65) Prior Publication Data
US 2018/0292383 A1    Oct. 11, 2018

(30) Foreign Application Priority Data

Apr. 30, 2015    (KR) .................. 10-2015-0061062

(51) Int. Cl.
*G01N 33/49*    (2006.01)
*A61B 5/00*    (2006.01)
(Continued)

(52) U.S. Cl.
CPC .............. *G01N 33/492* (2013.01); *A61B 5/00* (2013.01); *A61B 5/1468* (2013.01);
(Continued)

(58) Field of Classification Search
CPC ............. G01N 33/492; G01N 33/6893; G01N 33/48792; G01N 27/02; G01N 33/66;
(Continued)

(56) References Cited

U.S. PATENT DOCUMENTS

2011/0166792 A1* 7/2011 Takahata ................ G16H 50/50
702/19
2012/0197621 A1* 8/2012 Jain ........................ G16H 50/50
703/11

FOREIGN PATENT DOCUMENTS

KR    10-2002-0093150 A    12/2002
KR    20-0412556 Y1    3/2006
(Continued)

OTHER PUBLICATIONS

Xu et al. Biosensors and Bioelectronics, 39 (2013) 21-25. (Year: 2013) (Year: 2013) (Year: 2013) (Year: 2013).*
(Continued)

*Primary Examiner* — Sally A Merkling
(74) *Attorney, Agent, or Firm* — Revolution IP, PLLC

(57) ABSTRACT

A portable insulin resistance diagnosis device includes: a housing capable of being grasped by an outer periphery
(Continued)

thereof and comprising a space formed therein; a sensor unit which protrudes towards the outside of the housing and detects glucose and proteins in blood when a blood sample of a target specimen is dropped on the sensor unit, a diagnosis unit, which is provided inside the housing, amplifying an electrical signal generated according to concentrations of the blood glucose and proteins detected in the sensor unit, converting the electrical signal into a digital signal, and determining whether insulin resistance is normal; and a display unit, which is provided on an external surface of the housing, displaying whether insulin resistance analyzed in the diagnosis unit is normal.

8 Claims, 9 Drawing Sheets

(51) Int. Cl.
*A61B 5/145* (2006.01)
*A61B 5/1468* (2006.01)
*G01N 33/66* (2006.01)
*G01N 27/02* (2006.01)
*G01N 33/487* (2006.01)
*G01N 33/68* (2006.01)
*G01N 27/327* (2006.01)

(52) U.S. Cl.
CPC ......... *A61B 5/14532* (2013.01); *G01N 27/02* (2013.01); *G01N 33/48792* (2013.01); *G01N 33/66* (2013.01); *G01N 33/6893* (2013.01); *G01N 27/3273* (2013.01); *G01N 2800/042* (2013.01)

(58) Field of Classification Search
CPC .......... G01N 27/3273; G01N 2800/042; A61B 5/1468; A61B 5/14532; A61B 5/00
See application file for complete search history.

(56) References Cited

FOREIGN PATENT DOCUMENTS

| KR | 10-2010-0008260 A | 1/2010 |
|----|-------------------|--------|
| KR | 10-2012-0103911 A | 9/2012 |
| KR | 10-2014-0108810 A | 9/2014 |
| KR | 10-2014-0132869 A | 11/2014 |
| KR | 10-2014-0143999 A | 12/2014 |

OTHER PUBLICATIONS

Xiang et al. Journal of Diabetes Science and Technology, 2014 vol. 8(4) 855-858. (Year: 2014) (Year: 2014) (Year: 2014) (Year: 2014).*
Pinho et al. Biochip J. (2013) 7(4): 367-374. (Year: 2013) (Year: 2013) (Year: 2013) (Year: 2013).*
Singh et al. J Clin Res Pediatr Endocrinol 2013; 5 (4): 245-251 (Year: 2013) (Year: 2013) (Year: 2013) (Year: 2013).*
Accu CHeck Aviva Manual by ROche (Year: 2013).*
International Search Report for PCT/KR2016/004551 dated Aug. 29, 2016 from Korean Intellectual Property Office.
Kim, Ji Hoon et al., "Assessment of Insulin Resistance and Its Clinical Application", Journal of Korean Society of Endocrinology, vol. 24, No. 2, Jun. 30, 2009.
Santos et al., "Fundamentals and Applications of Impedimetric and Redox Capacitive Biosensors", Journal of Analytical & Bioanalytical & Bioanalytical Techniques, 2014, S7:016, Jun. 2, 2014.
Dimov et al., "Stand-alone self-powered integrated microfluidic blood analysis system (SIMBAS)", Lab on a Chip, 2011, vol. 11, No. 5, Mar. 7, 2011.
Christopher M.A. Brett et al., "Poly(methylene blue) modi®ed electrode sensor for haemoglobin", Analytica Chimica Acta 385 (1999) 119-123.

* cited by examiner

[FIGURE 1]
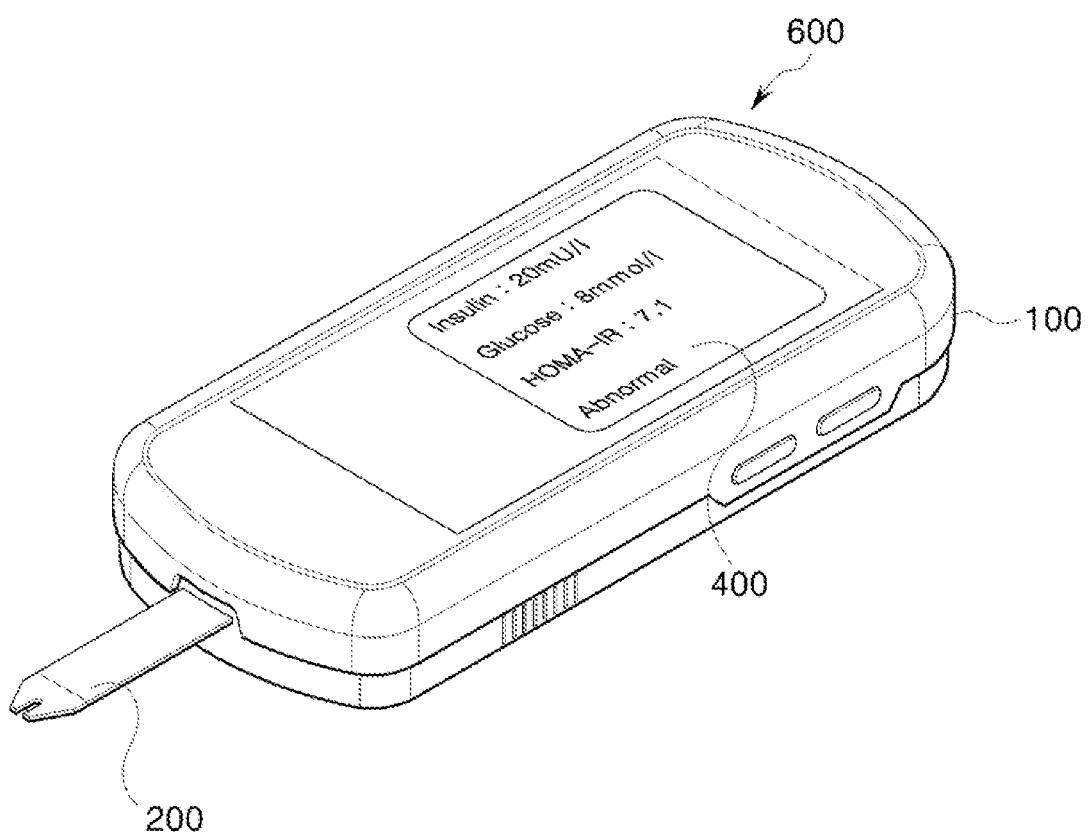

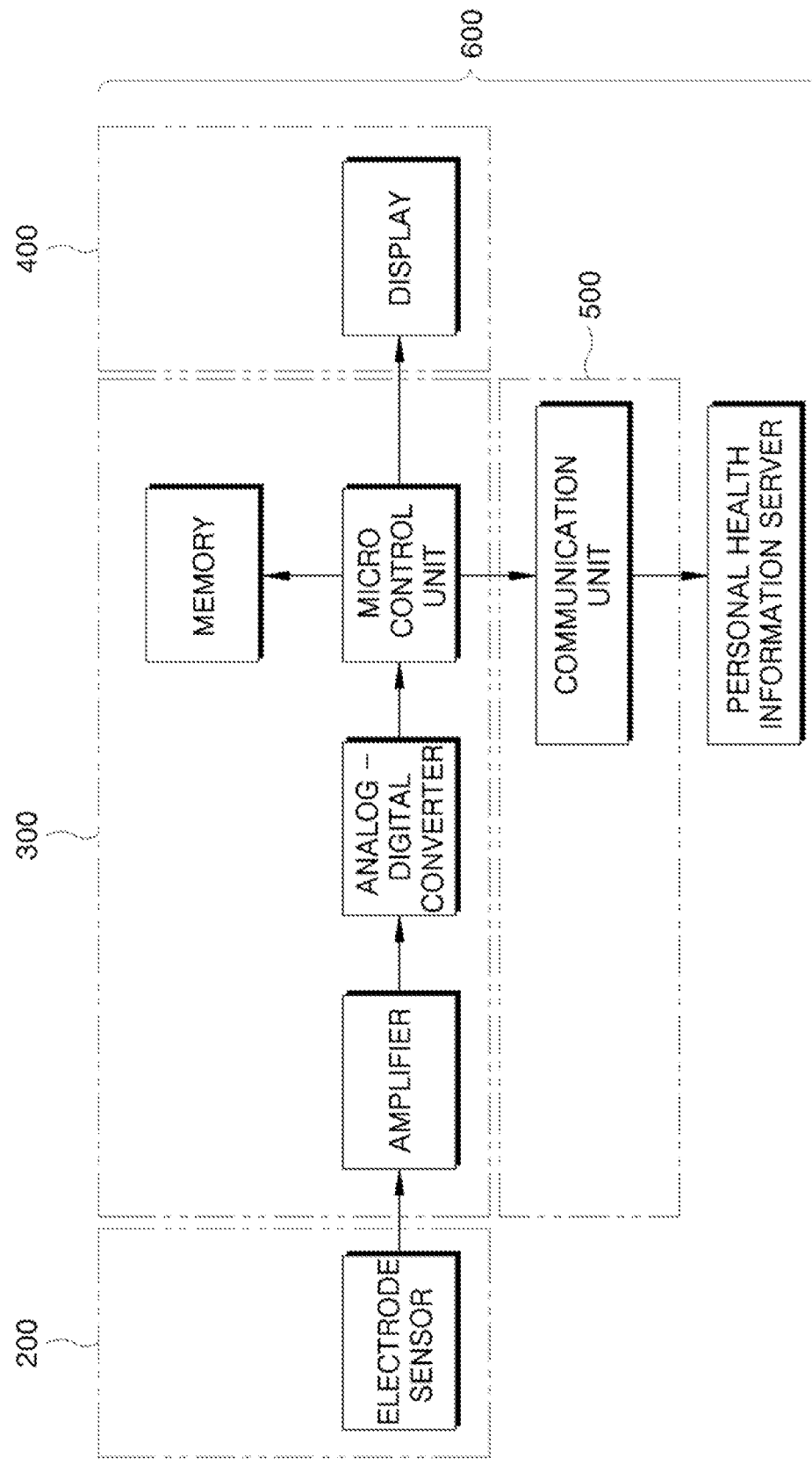
[FIGURE 2]

[FIGURE 3]
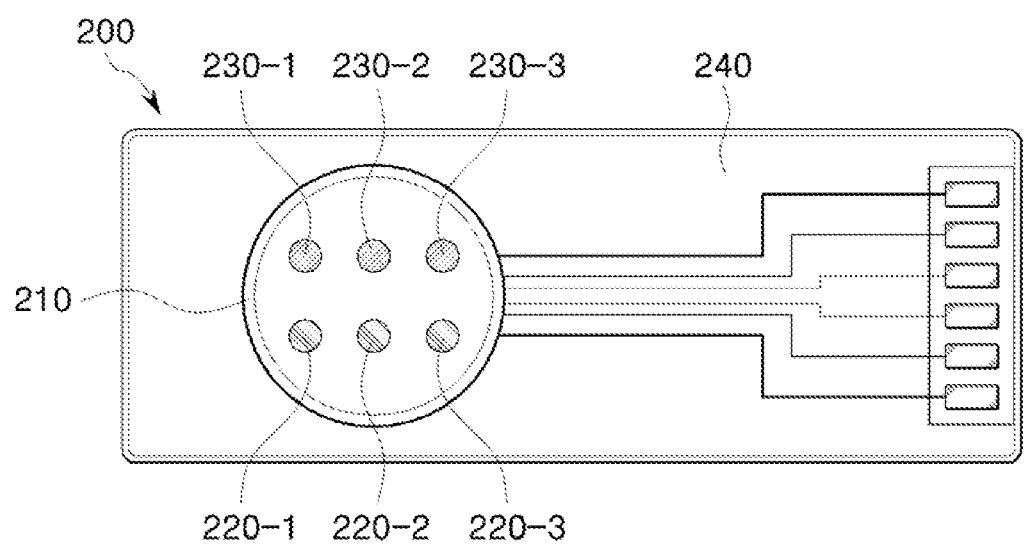

[FIGURE 4]
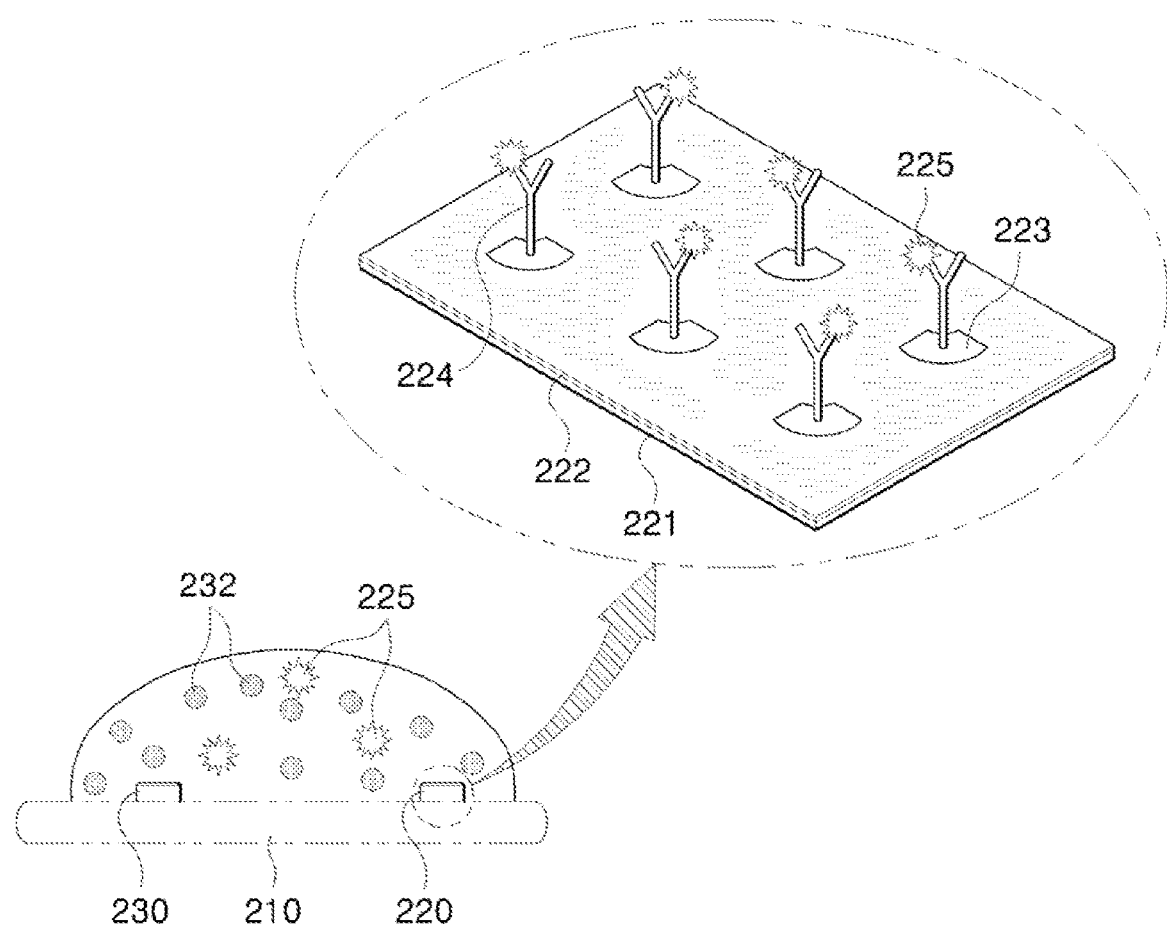

[FIGURE 5]
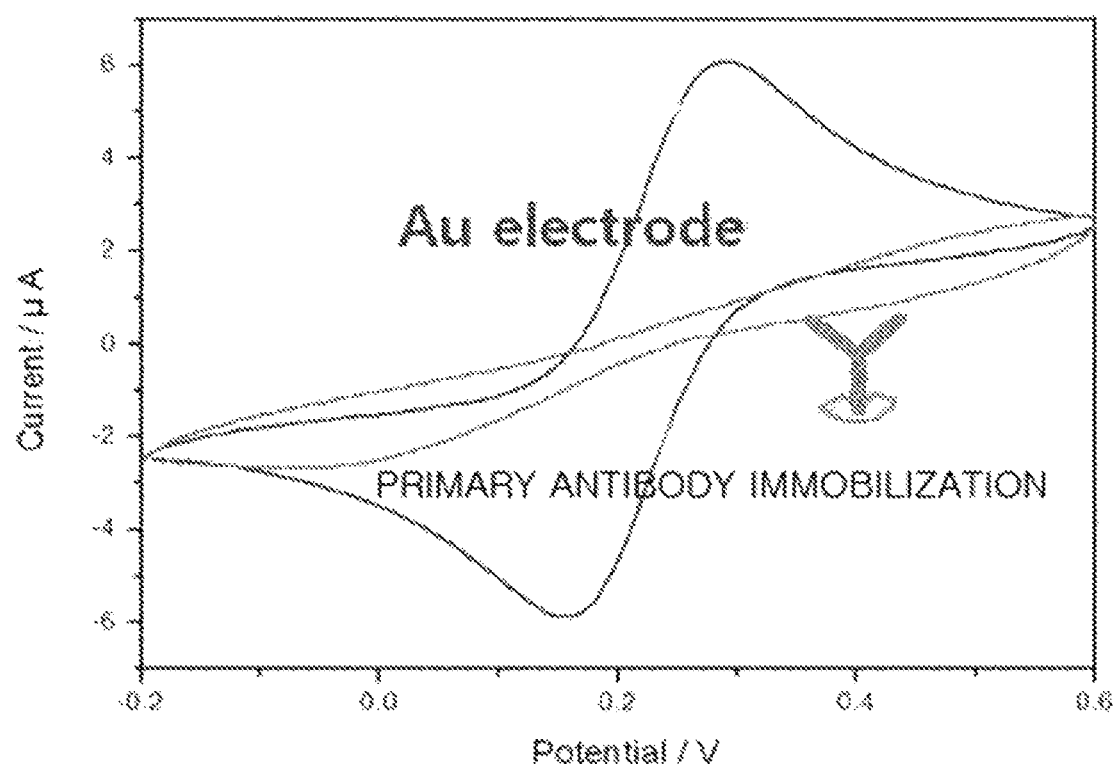

[FIGURE 6]
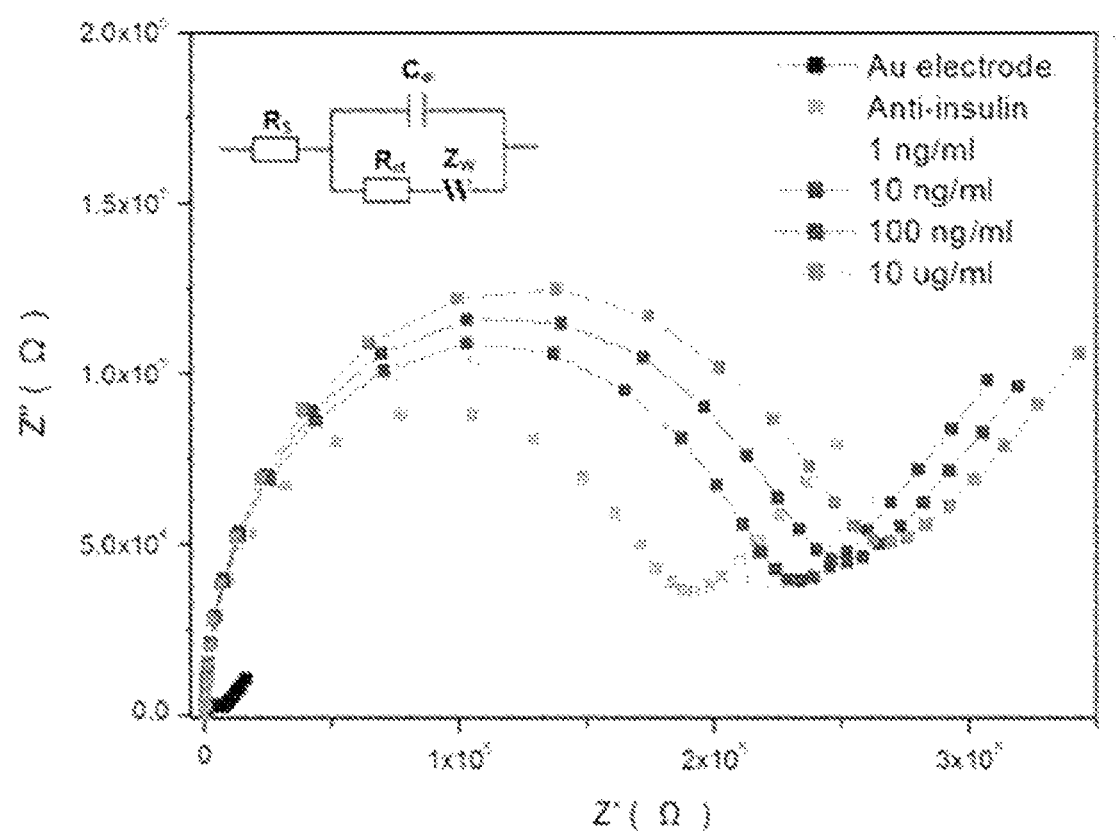

[FIGURE 7]
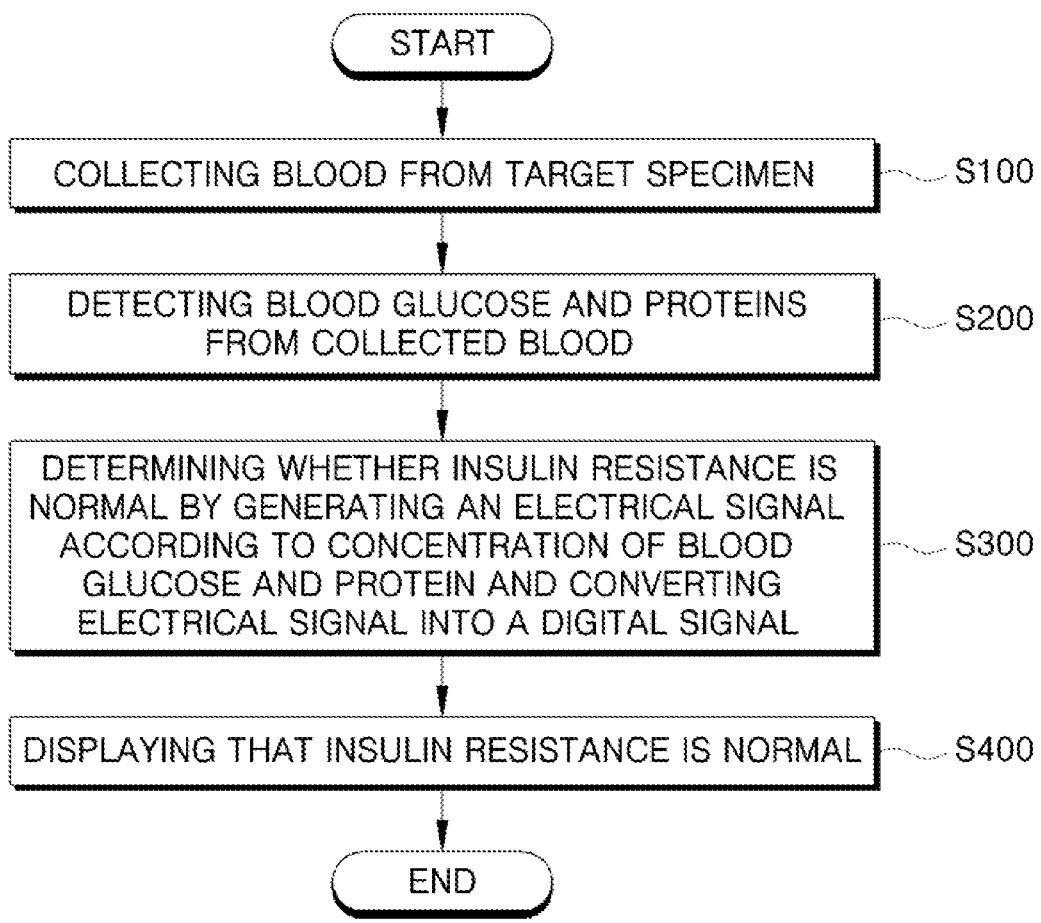

[FIGURE 8]
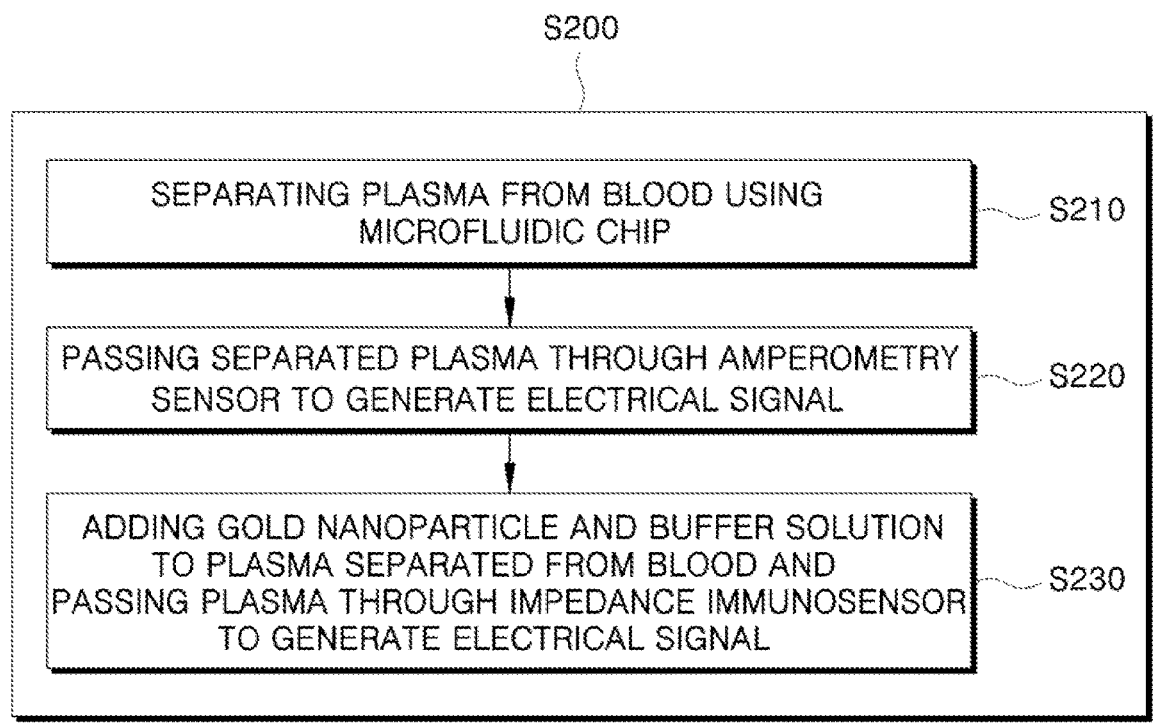

[FIGURE 9]
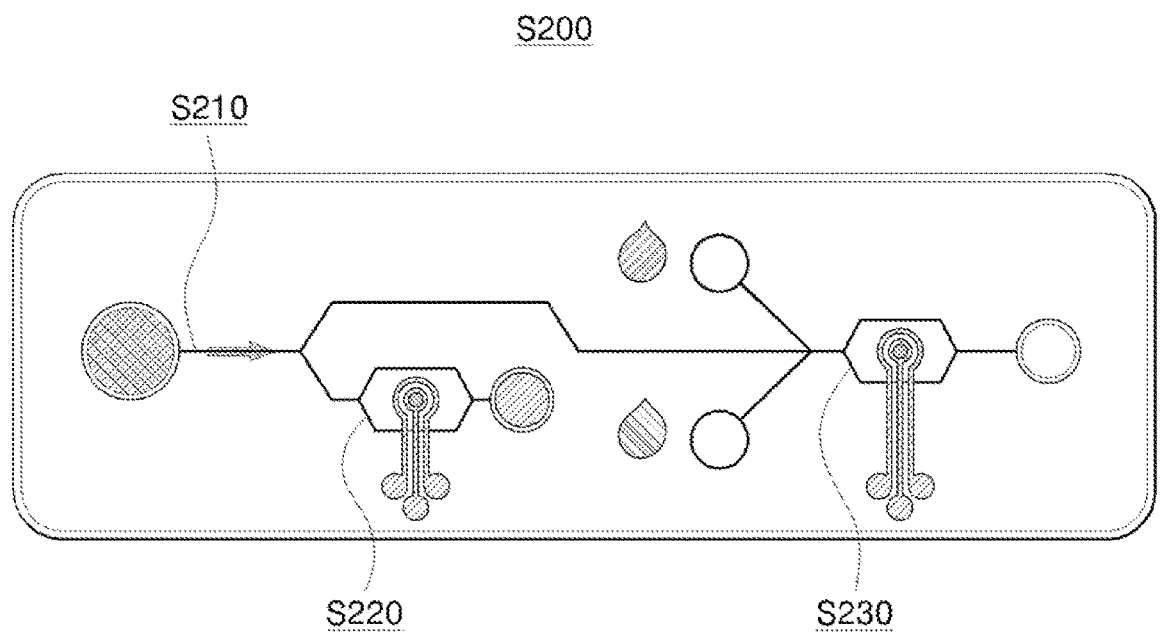

PORTABLE INSULIN RESISTANCE DIAGNOSIS DEVICE AND DIAGNOSIS METHOD USING SAME

TECHNICAL FIELD

The present invention relates to an insulin resistance diagnosis device capable of diagnosing insulin resistance and a diagnosis method using the same.

BACKGROUND ART

An insulin resistance syndrome is a cluster syndrome in which two or more clinical features, such as decrease in glucose metabolism, resistance against use of glucose, hyperinsulinemia, impared glucose tolerance, hyperglycemia, hypertension, increase in triglyceride, decrease in HDL-cholesterol, and the like, are present in a complex aspect, and is named 'syndrome X' or 'insulin resistance syndrome (IRS)', 'multiple metabolic syndrome (MMS)', or 'metabolic syndrome'.

When the insulin resistance syndrome is continued, secretion of insulin decreases as insulin secretion reaches its limit. Accordingly, a postprandial increase of blood glucose is not suppressed, and a fasting blood glucose level is increased beyond a normal range. If insulin is not secreted sufficiently enough to overcome insulin resistance, insulin resistance develops to an impaired glucose tolerance state. In addition, when deficiency in insulin secretion becomes severe, insulin resistance develops to diabetes with persistent hyperglycemia. Insulin resistance, which is a main clinical syndrome in common among the insulin resistance syndrome, refers to a condition in which a patient is less responsive to insulin than a normal person at a given concentration of insulin, i.e., a condition where functions of carrying and transporting glucose into tissues and utilizing glucose are degraded. Here, in terms of an insulin compensation action, the secretion of insulin is further stimulated in a pancreas, leading to an increase in a concentration of plasma insulin. Therefore, hyperinsulinemia caused by insulin resistance has been emphasized as a main cause of risk factors for type 2 diabetes, obesity, hypertension, hyperlipidemia, cardiovascular disorders including morbid obesity, and the like.

In particular, in the case of type 2 diabetes, type 2 diabetes is mainly caused by decreased secretion of insulin and insulin resistance. In Korea, type 2 diabetes is the most common disease. Regarding an insulin resistance testing method being conducted in major domestic hospitals, there is no accurate diagnosis method, but insulin resistance is determined by considerable insight of a medical staff based on tests on triglyceride and blood pressure performed in addition to the measurement of blood glucose or insulin level.

Regarding the measurement of insulin level, radioimmunoassay which checks insulin levels after 6 to 8 hours of fasting is carried out. Insulin resistance is diagnosed when the measured insulin level is higher than 60 pmol/L which is an average level of a normal person. However, the blood glucose level of patients with insulin resistance is mostly measured high in all cases after fasting or meal, and thus, accurate determination of insulin resistance is difficult.

Meanwhile, the Korean Patent Application No. 2002-7015204 relates to an agent for preventing insulin resistance or obesity and a method of screening insulin resistance or obesity, and more particularly, to a method of screening insulin resistance based on a fact that a compound capable of inhibiting a function of a gastric inhibitory polypeptide (GIP) or a glucose dependent Insulinotropic polypeptide can improve insulin resistance. However, there is no disclosure of a device capable of determining insulin resistance not using a receptor inhibitor, such as a GIP, but using blood only, and a method of determining insulin resistance.

DETAILED DESCRIPTION OF THE INVENTION

Technical Problem

The present invention aims to provide an insulin resistance diagnosis device and a method of diagnosing insulin resistance, for rapid and accurate diagnosis of an insulin resistance syndrome.

Technical Solution

To achieve the technical problem above, the present invention provides a portable insulin resistance diagnosis device including: a housing capable of being grasped by an outer periphery thereof and comprising a space formed therein; a sensor unit which protrudes towards the outside of the housing and detects glucose and proteins in blood when a blood sample of a target specimen is dropped on the sensor unit, the sensor unit comprising: a non-conductive substrate, a protein electrode sensor provided on the non-conductive substrate, a blood glucose electrode sensor provided on the non-conductive substrate but independently of the protein electrode sensor, and a circuit substrate extended at one side of each of the protein electrode sensor and the blood glucose electrode sensor; a diagnosis unit, which is provided inside the housing, amplifying an electrical signal generated according to concentrations of the blood glucose and proteins detected in the sensor unit, converting the electrical signal into a digital signal, and determining whether insulin resistance is normal; and a display unit, which is provided on an external surface of the housing, displaying whether insulin resistance analyzed in the diagnosis unit is normal.

Advantageous Effects of the Invention

According to the portable insulin resistance diagnosis device of the present invention, insulin resistance can be rapidly and accurately determined by collecting a small amount of blood of a specimen. Considering that insulin resistance can be referred to determine an insulin resistance syndrome, when insulin resistance is diagnosed, the prognosis of a disease progressing from an insulin resistance syndrome to type 2 diabetes can be accurately diagnosed. In addition, considering a non-invasive testing method and increased portability of the device, insulin resistance can be rapidly determined anywhere, thereby increasing convenience to patients. In addition, an insulin resistance diagnosis chip with high sensitivity to insulin is provided so that the reliability of a medical staff in determining insulin resistance can be ensured.

DESCRIPTION OF THE DRAWINGS

FIG. 1 is a perspective view of an insulin resistance diagnosis device according to an embodiment of the present invention.

FIG. 2 is a block diagram illustrating a configuration of the insulin resistance diagnosis device according to an embodiment of the present invention.

FIG. 3 is a plan view of a sensor unit of the insulin resistance diagnosis device of FIG. 1.

FIG. 4 is a side view of a protein electrode sensor and a blood glucose electrode sensor of the insulin resistance diagnosis device of FIG. 1 and a schematic enlarged view of the protein electrode sensor.

FIG. 5 is a graph based on cyclic voltammetry after a gold-doped electrode of an impedance immunosensor according to an embodiment of the present invention is immobilized with a protein G multimer.

FIG. 6 shows a spectrum obtained by electrochemical impedance spectroscopy after a gold-doped electrode of an impedance immunosensor according to an embodiment of the present invention is immobilized with a protein G multimer.

FIG. 7 is a flow chart showing a sequence of a method of diagnosing insulin resistance according to an embodiment of the present invention.

FIG. 8 is a flowchart showing a step of detecting blood glucose and proteins according to FIG. 7.

FIG. 9 is a schematic view showing a step of detecting of blood glucose and proteins according to FIG. 7.

BEST MODE

Hereinafter, preferable embodiments of the present invention will be described in detail by referring to the accompanying figures.

FIG. 1 is a perspective view of an insulin resistance diagnosis device according to an embodiment of the present invention, FIG. 2 is a block diagram illustrating a configuration of the insulin resistance diagnosis device according to an embodiment of the present invention, FIG. 3 is a plan view of a sensor unit of the insulin resistance diagnosis device of FIG. 1, and FIG. 4 is a side view of a protein electrode sensor and a blood glucose electrode sensor of the insulin resistance diagnosis device of FIG. 1 and a schematic enlarged view of the protein electrode sensor.

Referring to the figures, a portable insulin resistance diagnosis device 600 of the present invention includes a housing 100, a sensor unit 200, a diagnosis unit 300, and a display unit 400.

A surface of the housing 100 is smoothly treated so that a medical staff or a patient who checks a diabetes condition every day can carry it easily and also easily grasp it by a hand. In addition, the housing 100 provides a space therein where the diagnosis unit 300 can be provided.

The sensor unit 200 includes a non-conductive substrate 210, a protein electrode sensor 220, a blood glucose electrode sensor 230, and a circuit substrate 240.

In addition, the sensor unit 200 protrudes towards the outside of the housing 100, and can detect glucose and proteins in blood when a blood sample of a target specimen is dropped thereon. The sensor unit 200 protrudes towards the outside of the housing 100 when the blood is dropped thereon. However, when insulin resistance is not subjected to diagnosis, the sensor unit 200 can be slid into the housing 100 and accommodated therein. When the sensor unit 200 is accommodated inside the housing 100, the portability of the portable insulin resistance diagnosis device can be increased.

The protein may be insulin or c-peptide.

When the protein is c-peptide, insulin resistance may be determined according to the conventional evaluation index of endogenous secretion ability of insulin. However, when the protein is insulin, insulin resistance may be directly determined based on a concentration of insulin.

The non-conductive substrate 210 may serve as a substrate on which the protein electrode sensor 220 and the blood glucose electrode sensor 230 are disposed and immobilized. Considering bonding of a gold-doped electrode to the protein electrode sensor 220, an electrode may be formed of polyvinylchloride (PVC) that can be doped with gold, but embodiments of the present invention are not limited thereto.

The protein electrode sensor 220 may include an inlet 220-1, 220-2, or 220-3, a microfluidic chip (not shown), an injection well, and an impedance immunosensor (not shown).

Here, the inlet 220-1, 220-2, or 220-3 may deliver blood introduced thereto into the protein electrode sensor 220, and may be provided in multiple.

The protein electrode sensor 220 including the inlet may be sequentially distinguished as a working electrode 220-1, a counter electrode 220-2, and a reference electrode 220-3.

The microfluidic chip may include a plurality of microchannels, and transfers plasma only to the impedance immunosensor, except for formed elements of blood, such as erythrocytes, leukocytes, and platelets.

Since insulin detected by the protein electrode sensor 220 is present in plasma of blood, a process of separating plasma through the microchannels of the microfluidic chip may increase the accuracy of insulin detection. If the microfluidic chip is not provided, not only the accuracy of the insulin detection by the protein electrode sensor 220 may be reduced, but also the sensitivity of the portable insulin resistance diagnosis device 500 may be reduced.

The injection well may supply a buffer solution to the plasma discharged from the microfluidic chip, wherein the buffer solution to be added to the injection well may be a 1.0 M phosphate buffer solution having pH 7.0 to pH 0.05. However, the buffer solution is not limited thereto, so long as a nanoparticle can bind to insulin to form a complex.

In addition, the injection well may supply a buffer solution to the plasma discharged from the microfluidic chip, and the nanoparticle may be a gold nanoparticle.

When the nanoparticles is a gold nanoparticle, the gold nanoparticle may be dispersed in the buffer solution, and then, bind to insulin to form a nanocomposite. In the case of forming such a nanocomposite, the sensitivity of an antigen-antibody reaction, which will be described later, i.e., a reaction between insulin and an anti-insulin antibody, may be increased. In this regard, the antibody-antigen steric hindrance may be decreased, and accordingly, insulin may accurately bind to the impedance immunosensor.

Here, the impedance immunosensor may include an insulin antigen, i.e., a nanocomposite (not shown), to which a gold-doped electrode 221, or 222, a protein G multimer 223, an anti-insulin antibody 224, and a gold nanoparticle are bound.

In addition, when the impedance immunosensor detects c-peptide, monoclonal anti-c-peptide, as well as the protein G multimer 223, may be bound to the impedance immunosensor.

The gold-doped electrode 221 or 222 may be immobilized with the protein G multimer 223.

When the protein G multimer 223 is immobilized with the gold-doped electrode 221 or 222, a site where the protein G multimer 223 can bind to plasma insulin may be provided. In particular, when a nanocomposite formed by binding between insulin and a gold nanoparticle binds to the protein G multimer 223, an antigen-antibody reaction in which insulin (as an antigen) and anti-insulin (as an antibody) are bound may occur.

FIG. 5 is a graph based on cyclic voltammetry after the gold-doped electrode of the impedance immunosensor according to an embodiment of the present invention is immobilized with the protein G multimer.

Referring to FIG. 5, the graph is obtained by measurement under conditions where a voltage ranges from −0.2 V to 0.6 V and a scanning rate is 0.1 V/s. The gold-doped electrode is observed to have a low initiation potential value and a large width of a voltage-dependent current change. However, when being immobilized with the protein G multimer, the initiation potential value is increased while the width of the voltage-dependent current change is reduced.

Therefore, when the electrode is doped with gold, it is confirmed that the protein G multimer binds thereto such that the surface of the electrode is modified. Accordingly, the result shows that the protein G multimer, which is an antibody, is successfully immobilized.

When the electrode is doped with gold, without using an additional enzyme, an insulin-bound nanocomposite can be immobilized with the electrode, and accordingly, the detection range of insulin may be greatly increased.

Here, phenylene diisothiocyanate (PDITC) may be mixed with cysteamine, and the protein G multimer 223 may be bound to the gold-doped protein G multimer 223 in the same manner as the addition of the protein G multimer 223 described above.

FIG. 6 shows a spectrum obtained by electrochemical impedance spectroscopy after the gold-doped electrode of the impedance immunosensor according to an embodiment of the present invention is immobilized with the protein G multimer.

Referring to FIG. 6, the frequency range is set to 0.001 Hz to 10 kHz, the direct voltage is set to 0.23 V, and the potential amplitude is set to 0.01 V. As a result of measuring impedance on the gold-doped electrode and the gold-doped electrode immobilized with the protein G multimer, it is found that impedance is almost not measured at the purely gold-doped electrode, whereas impedance increases when the anti-insulin antibody is immobilized with the gold-doped electrode. In particular, when the concentration of insulin is increased from 1 ng/mL to 10 ug/mL, the impedance value is also quantitatively increased. Accordingly, it is confirmed that the impedance value changes are dependent upon the concentrations of plasma insulin and can be quantified.

The impedance immunosensor can quantitatively measure the concentrations of plasma insulin by measuring the impedance of the nanocomposite that is attached to the electrode, and then, by converting the measured impedance into an electrical signal, so as to transmit the electrical signal to the circuit substrate 240.

Meanwhile, the blood glucose electrode sensor 230 may be provided on the non-conductive substrate 210 independently of the protein electrode sensor 220. Here, the non-conductive substrate 210 may serve as a substrate on which the blood glucose electrode sensor 230 is disposed and immobilized.

The blood glucose electrode sensor 230 may include an inlet 230-1, 230-2, or 230-3, a microfluidic chip (not shown), and an amperometry sensor (not shown).

The inlet 230-1, 230-2, or 230-3 and the microfluidic chip are the same as those described above, and thus repetitive descriptions thereof will be omitted.

The amperometry sensor can measure a concentration of blood glucose. The concentration of blood glucose can be measured by measuring an electron generated by oxidation of plasma glucose and by converting an electron into a current. Here, depending on the concentration of blood glucose, a change of the current may be measured. The amperometry sensor may convert the current into an electrical signal, and then, may transmit the electrical signal to the circuit substrate 240.

The circuit substrate 240 may be electrically communicated with the diagnosis unit 330, so as to transmit the electrical signal generated from the protein electrode sensor 220 and the blood glucose electrode sensor 230 to the diagnosis unit 300.

The diagnosis unit 300 is provided in the housing 100, and amplifies an electrical signal according to the concentrations of blood glucose and proteins that are detected by the sensor unit 200. The diagnosis unit 300 also converts the amplified electrical signal into a digital signal, so as to determine whether insulin resistance is normal or not.

Regarding the concentrations of blood glucose and proteins that are detected by the sensor unit 200, an electrical signal is converted according to the concentrations of blood glucose and proteins at the impedance immunosensor and the amperometry sensor to be transmitted to the diagnosis unit 300 via the circuit substrate 240.

FIG. 2 is a block diagram illustrating a configuration of an insulin resistance diagnosis device according to an embodiment of the present invention.

Referring to FIG. 2, the diagnosis unit 300 may include an amplifier, an analog-digital converter, a memory, and a microcontrol unit.

The amplifier amplifies the electrical signal and transmits the amplified electrical signal to the analog-digital converter. Then, the analog-digital converter converts the electrical signal into a digital signal of a quantitative value, and transmits the quantitative value to the microcontrol unit.

The microcontrol unit receives the digital signal and calculates a numerical value, and a quantitative concentration according to the numerical value is calculated according to the equation below. The microcontrol unit can then determine insulin resistance according to the value obtained by the equation below:

$$HOMA-IR = \frac{POSTPRANDIAL\ BLOOD\ GLUCOSE(mM/L) \times POSTPRANDIAL\ BLOOD\ INSULIN(IU/mL)}{22.5}$$
[Equation]

Here, HOMA-IR is a constant indicating the result of the equation.

The value of postprandial blood glucose is obtained by converting the electrical signal, which is generated according to the concentration of glucose at the blood glucose electrode sensor 230, at the analog-digital converter, and the value of the postprandial blood insulin is obtained by converting the electrical signal, which is generated according to the concentration of insulin at the protein electrode sensor 220, at the analog-digital converter.

The microcontrol unit may then determine that insulin resistance is abnormal, when the result of the equation above exceeds 3.

The display unit 400 is provided on an outer surface of the housing 100, and can display whether the insulin resistance analyzed in the diagnosis unit 300 is normal along with the concentrations of blood glucose and proteins detected in the sensor unit 200.

Referring to FIG. 1, the display unit 400 displays the concentrations of blood glucose and proteins and the HOMA-IR value, and also indicates whether the insulin resistance is normal.

In addition, when a protein to which the protein electrode sensor 220 binds is a c-peptide, the display unit 400 displays a concentration of the c-peptide. In the case where the concentration of the c-peptide is detected and displayed, the secretion of insulin of a target specimen can be confirmed.

In addition, the insulin resistance diagnosis device 200 may further include a communication unit on one inner side of the housing 100.

The communication unit transmits the insulin resistance value determined by the diagnosis unit 300 to an external personal health information server.

Such a personal health information server may collect and save information provided from a plurality of insulin resistance diagnosis devices. When the insulin resistance is determined to be abnormal through simple blood collection, the insulin resistance may be periodically determined and saved. In addition, by monitoring changes in the insulin resistance saved in the personal health information sever, the prognosis of insulin resistance syndrome which progresses to diabetes can be observed.

According to another aspect of the present invention, there is provided a method of diagnosing insulin resistance, the method including: collecting blood from a target specimen; detecting blood glucose and proteins from the collected blood; determining whether insulin resistance is normal by generating an electrical signal according to concentrations of the blood glucose and proteins and converting the electrical signal into a digital signal; and displaying whether the insulin resistance is normal.

FIG. 7 is a flow chart showing a sequence of the method of diagnosing insulin resistance according to an embodiment of the present invention.

Referring to FIG. 7, first, blood can be collected from a target specimen (S100).

Considering that glucose and insulin can be measured from the collected blood, blood may be dropped into the sensor unit and blood glucose and proteins can be detected from the collected blood (S200).

FIG. 8 is a flowchart showing a step of detecting blood glucose and proteins according to FIG. 7, and FIG. 9 is a schematic view showing a step of detecting of blood glucose and proteins according to FIG. 7.

Referring to FIGS. 8 and 9, the detecting of blood glucose and proteins (S200) includes: separating plasma from blood using a microfluidic chip (S210); passing the separated plasma through an amperometry sensor to generate an electrical signal (S220); and adding a gold nanoparticles and a buffer solution to the plasma separated from the blood and passing the plasma through an impedance immunosensor to generate an electrical signal (S230).

The microfluidic chip can remove a formed element of blood through a microchannel for separation of the plasma, and then, can introduce the separated plasma to the amperometry sensor, thereby increasing the measurement sensitivity of the blood glucose and insulin.

The amperometry sensor can generate an electrical signal according to a method of converting an electron into a current, wherein the electron is emitted by oxidizing glucose in the plasma introduced thereto (S220).

A part of the plasma may be introduced to the impedance immunosensor. Before the introduction of the plasma to the impedance immunosensor, a nanoparticles and a buffer solution may be introduced to the impedance immunosensor, wherein the nanoparticles may be a gold nanoparticles, and the buffer solution may be a phosphate buffer solution contained in the plasma.

When the gold nanoparticles and the phosphate buffer solution are added to the flow of the plasma, the gold nanoparticles and plasma insulin may bind to each other, thereby forming a nanocomposite. Such a nanocomposite binds to the protein G multimer attached on the gold-doped electrode, and accordingly, the insulin in the nanocomposite may be fixed on the gold-doped electrode.

When the insulin is attached on the gold-doped electrode, the impedance of the electrode changes, and such a change in the impedance can generate an electrical signal (S230).

Next, the electrical signal is converted into a digital signal, and transmitted to a step of determining whether insulin resistance is normal (S300).

In the step S300 of determining whether the insulin resistance is normal, a result is calculated according to the equation below. The insulin resistance is determined to be abnormal when the result of the equation below exceeds 3.

$$HOMA - IR = \frac{\text{POSTPRANDIAL BLOOD GLUCOSE(mM/L)} \times \text{POSTPRANDIAL BLOOD INSULIN(IU/mL)}}{22.5}$$ [Equation]

Here, HOMA-IR indicates a constant value as a result of the Equation.

As described above, according to the portable insulin resistance diagnosis device and the diagnosis method according to the present invention, early diagnosis of insulin resistance is possible, and the concentrations of blood glucose and insulin can be quantitatively measured to determine and indicate insulin resistance, thereby accurately diagnosing the prognosis of a disease in which insulin resistance progresses to insulin resistance syndrome.

While one or more embodiments have been described with reference to the figures, it should be understood by those of ordinary skill in the art that embodiments described herein should be considered in a descriptive sense only and not for purposes of limitation, and that various changes in form and details may be made therein without departing from the spirit and scope as defined by the following claims.

| | |
|---|---|
| 100: HOUSING | 200: SENSOR UNIT |
| 210: NON-CONDUCTIVE SUBSTRATE | |
| 220: PROTEIN ELECTRODE SENSOR | |
| 221: SUBSTRATE | 222: GOLD-DOPED |
| 223: PROTEIN G MULTIMER | 225: INSULIN |
| 230: BLOOD GLUCOSE ELECTRODE SENSOR | |
| 232: GLUCOSE | |
| 240: CIRCUIT SUBSTRATE | 300: DIAGNOSIS UNIT |
| 400: DISPLAY UNIT | |

The invention claimed is:

1. A portable insulin resistance diagnosis device comprising:
   a housing capable of being grasped by an outer periphery thereof and comprising a space formed therein;
   a sensor unit which protrudes towards the outside of the housing and detects glucose and proteins in blood when a blood sample of a target specimen is dropped on the sensor unit, the sensor unit comprising: a non-conductive substrate, a protein electrode sensor provided on the non-conductive substrate, a blood glucose electrode sensor provided on the non-conductive substrate but independently of the protein electrode sensor, and a circuit substrate extended at one side of each of the protein electrode sensor and the blood glucose electrode sensor;

a diagnosis unit configured and executed by a processor, the diagnosis unit provided inside the housing, comprising:

an amplifier amplifying an electrical signal generated according to concentrations of the blood glucose and proteins detected in the sensor unit;

an analog-digital converter converting the electrical signal into a digital signal; and a microcontrol unit receiving the digital signal and being configured to determine insulin resistance according to the result of an equation, wherein the processor is configured to output a normal or abnormal result response according to the result of the equation; and a display unit, which is provided on an external surface of the housing, displaying the insulin resistance analyzed in the diagnosis unit, wherein the protein electrode sensor comprises an inlet to which blood is injected, a microfluidic chip which separates plasma from the injected blood, an injection well for adding a nanoparticle and a buffer solution to the plasma, and an impedance immunosensor.

2. The portable insulin resistance diagnosis device of claim 1, further comprising a communication unit formed on one inner side of the housing and transmitting a value of insulin resistance determined in the diagnosis unit to an external personal health information server.

3. The portable insulin resistance diagnosis device of claim 1, wherein the display unit displays the insulin resistance analyzed in the diagnosis unit and also indicates concentrations of blood glucose and proteins detected in the sensor unit, respectively.

4. The portable insulin resistance diagnosis device of claim 1, wherein the protein is insulin or c-peptide.

5. The portable insulin resistance diagnosis device of claim 1, wherein the impedance immunosensor comprises a gold-doped electrode, a protein G multimer immobilized on a surface of the gold-doped electrode, an anti-insulin antibody bound to the protein G multimer, and an insulin antigen including a gold nanoparticle bound thereto.

6. The portable insulin resistance diagnosis device of claim 1, wherein the blood glucose electrode sensor comprises an inlet to which blood is injected, a microfluidic chip which separates plasma from the injected blood, and an amperometry sensor which measures a change in a current generated by oxidation of plasma glucose.

7. The portable insulin resistance diagnosis device of claim 1, wherein the microcontrol unit determines whether the insulin resistance is the normal or abnormal result response according to the result of the equation below with respect to a quantitative concentration dependent upon a numerical value that is calculated by receiving the digital signal:

$$HOMA - IR = \frac{\text{POSTPRANDIAL BLOOD GLUCOSE(mM/L)} \times \text{POSTPRANDIAL BLOOD INSULIN(IU/mL)}}{22.5}, \quad \text{[Equation]}$$

wherein, HOMA-IR is a constant as the result of the equation.

8. The portable insulin resistance diagnosis device of claim 7, wherein the microcontrol unit determines that the insulin resistance is the abnormal result response when the result of the equation is greater than 3.

* * * * *